United States Patent [19]

Han et al.

[11] 4,431,735

[45] Feb. 14, 1984

[54] BIOLOGICAL PROCESS FOR THE PREPARATION OF RIFAMYCIN DERIVATIVES

[75] Inventors: Moon H. Han; Tae-Ick Mheen; Baik L. Seong; Hyeung-Jin Son, all of Seoul, Rep. of Korea

[73] Assignee: Korea Advanced Institute of Science and Technology, Seoul, Rep. of Korea

[21] Appl. No.: 336,593

[22] Filed: Jan. 4, 1982

[51] Int. Cl.$^3$ .................. C12P 17/18; C12N 9/04; C12R 1/645

[52] U.S. Cl. .................. 435/119; 435/190; 435/911

[58] Field of Search .................. 435/119, 190

[56] References Cited

U.S. PATENT DOCUMENTS 3,871,965  3/1975  White et al. .................. 435/119
3,871,966  3/1975  Pasqualucci et al. .................. 435/119

Primary Examiner—Alvin E. Tanenholtz
Attorney, Agent, or Firm—Holman & Stern

[57] ABSTRACT

A biological process for converting rifamycin B to rifamycin O, rifamycin S or rifamycin SV by treatment with the whole cell, the cell extract, or the immobilized enzyme of *Humicola* spp. (ATCC 20620) or *Monocillium* spp. (ATCC 20621) is provided. The process also includes the recovery of rifamycin B in the fermentation broth after conversion to rifamycin O, rifamycin S or rifamycin SV.

7 Claims, No Drawings

BIOLOGICAL PROCESS FOR THE PREPARATION OF RIFAMYCIN DERIVATIVES

FIELD OF THE INVENTION

This invention relates to a process for the enzymatic preparation of rifamycin derivatives, especially rifamycin O, rifamycin S and rifamycin SV from rifamycin B.

BACKGROUND OF THE INVENTION

Rifamycins, which are a group of macrocylic hydroquinonequinone antibiotics having a close relationship to each other, are described in *Antibiotics Annual*, 262 (1959), *Appl. Microbiol.*, 9, 325 (1961), and *Progr. Ind. Microbiol*, 6, 21 (1967).

Rifamycin derivatives have been prepared by the chemical conversion of rifamycin B, which is an antibiotic produced by fermenting *Nocardia mediterranei*. Among these, rifamycin O and rifamycin S, the key intermediates for the synthesis of rifamycin derivatives are of great therapeutic use and, have been prepared from rifamycin B by chemical processes. Many efforts have been made for the improvement of this process, as can be seen from prior art such as the description of Japan Kokai No. 37-8,550, Japan Kokai 38-15,352, British Pat. No. 324,452, and German Pat. No. 2,444,527. Recovery of rifamycins from the fermentation broth has also been disclosed in many reports. Two kinds of recovery processes are known: as rifamycin B, in *Progr. Ind. Microbiol.*, 6,21 (1967); and as rifamycin O, in U.S. Pat. No. 3,847,903, French Patent No. 2,221,517, Netherlands Pat. No. 73-03,196, Japan Kokai No. 49-117,692, German Pat. No. 2,310,731, and South African Pat. No. 73-01,328. The recovery of rifamycin O is essentially based on the chemical oxidation of rifamycin B.

In general, the oxidation of rifamycin B to rifamycin O is carried out in an organic solvent or an organic solvent-water mixture. Artificial oxidants such as sodium nitrite, sodium persulfate or hydrogen peroxide are usually employed at a slightly acidic condition (pH 4.5). The hydrolysis of rifamycin O to rifamycin S also spontaneously occurs at a more acidic condition. The improved processes for the preparation of rifamycin S from rifamycin O are disclosed in British Pat. No. 924,472 and German Pat. No. 2,444,527. All the processes hitherto reported are essentially based on chemical processes which require artificial oxidants and a strong acidic condition, where the substantial formation of by-products cannot be obviated. Therefore, an enzymatic process is desirable, in which the conversion can be carried out with a quantitative yield due to the mild condition employed and the specificity of the enzyme.

BRIEF SUMMARY OF THE INVENTION

The primary object of the invention is to provide a process for the enzymatic preparation of rifamycin derivatives from rifamycin B.

Another object of the invention is to provide a process for the enzymatic preparation of rifamycin O from rifamycin B.

An additional object of the invention is to provide a process for the enzymatic preparation of rifamycin S from rifamycin B.

Still another object of the invention is to provide a process for the enzymatic preparation of rifamycin SV from the rifamycin B.

These and other objects can be achieved by the process of the invention which comprises subjecting the rifamycin B solution or the rifamycin B fermentaton broth to the action of the microbial oxidation enzyme selected from the group consisting of Humicola spp. (ATCC 20620) and Monocillium spp. (ATCC 20621). The enzyme may be in the form of any of the microbial cells, cell extract, adsorbed enzyme, whole cells, or immobilized enzyme. The process is performed at a temperature ranging from 20° to 50° C. and at a pH ranging from 4 to 9 for a sufficient time to convert rifamycin B to rifamycin O or rifamycin S.

When treating rifamycin B with the microbial oxidase, the predominating product is rifamycin O at a pH range of from 4 to 6, and rifamycin S at a pH range of from 6 to 9. Rifamycin S may conventionally be reduced to rifamycin SV in the presence of ascorbic acid.

After the reaction is completed, the respective desired products can be recovered as precipitates by virtue of the control of the pH value of the reaction medium.

DETAILED DESCRIPTION OF THE INVENTION

In view of the problems or disadvantages normally encountered in chemical processes, we have endeavored to find microbial species to catalyze the conversion of rifamycin B to rifamycin O or rifamycin S. It has now been found that by using two strains of fungi which have not yet been known, all of the disadvantages of the chemical process are obviated and a commercially more feasiable method for preparing rifamycin O and rifamycin S from rifamycin B is achieved. One of the new species was identified as Humicola spp., and has been deposited in the American Type Culture Collection (ATCC) in Washington, D.C., wherein it has been assigned the number ATCC 20620. The other new strain was identified as Monocillium spp. This microogranism has also been deposited in American Type Culture Collection, wherein it has been assigned the number ATCC 20621. These new strains can be assigned to respective genera by the following morphological and physiological characterisics as summarized in Tables I and II.

The enzyme activity is obtained by growing the desired microorganism in a nutrient medium for a sufficient time. On separating the microbial cells from the fermentation broth through filtration or centrifugation, the enzyme activity is found mainly in the cells, rather than in the broth. The enzyme responsible for the conversion of rifamycin B is an intracellular one by this discovery. In accordance with a preferred embodiment of this invention, the desired microorganism is grown in contact with a suitable nutrient medium in the presence of air. A suitable nutrient medium essentially comprises sources of nitrogenous factors and assimilable sources of carbon and energy with or without inorganic metal ions. The major carbon source includes a carbohydrate such as glucose, fructose, sucrose, maltose, starch, glycerin or dextrin. The source of nitrogenous factors includes organic materials, for example, soybean meal, corn steep liquor, meat extract, distiller's soluble, peptone, and/or yeast extract or synthetic materials, for example, those composed of simple, synthesizable organic and inorganic compounds such as ammonium salts, alkali nitrates or amino acids. The microorgnism is grown at a suitable temperature between 25° C. to 35° C. for a suitable period of time, preferably about two to four days in the presence of a source of oxygen, such as by shaking while exposing to air or agitation with air blowing. Although the culture may be used directly for the oxidation and hydrolysis of rifamycin B, in the preferred process of this invention, the supernatants are removed through filtration or centrifugation, and the microbial cells containing the major portion of the enzyme are used for the reaction. The microbial cells can be used directly as a whole cell enzyme. The cell extract obtained after disruption of whole cells and centrifugation may also be used as an enzyme source with or without freeze drying. The immobilized enzyme can also be used for a continuous process or repetitively used in a batch reaction. The immobilized enzyme can be prepared through the adsorption of the enzyme of the cell extract on silicate materials such as bentonite, celite, diatomaceous earth, kaolin, silica gel or other materials such as activated carbon or alumina. The entrappment of whole cells in acrylamide gel with or without defatting the cells by treatment with acetone can be used for the preparation of the immobilized enzyme.

TABLE I.

Morphological Observations

| Morphology | Strain | |
|---|---|---|
| | Humicola spp. ATCC 20620 | Monocillium spp. ATCC 20621 |
| Microscopic observations | When grown on YM agar medium at 30° C. for 4–6 days, conidiophores are simple or rarely with short branches, septate, and dark; conidia (aleuriospores) are single apical, globose or subglobose, brown and one-celled. | After 5–7 days of growth on YM agar medium at 30° C. conidiophores are septate, consisting of a pedical, and a swollen vesicle which bears a long chain of conidia formed basipetally; conidia (phialospores) are one-celled, hyalline, ovoid to ellipsoid, and smooth. |
| Malt extract agar plate | After 5 days, the colony is white and cerebriforme with velvety texture. As conidia develop, the colony becomes powdery. | A rapidly growing colony is white, flat and entire-edged. The texture is velvety. A dark green central zone and orange reverse color are developed after 5–7 days. |
| Czapek-Dox agar plate | The organism has a slow growth rate with a colony that is brownish white and flat. The texture is more or less glabrous. | The organism has a moderate growth rate with a colony that is white, flat and entire-edged. The texture is compact wooly. A greenish black color appears as conidia develop |
| Gelatin agar plate | The organism has a intermediate growth rate. A white, flat and velvety colony is developed. No pigment is produced. | The colony is flat and white with a slightly brown central zone. As conidia develop, a dark green color appears. The texture is compact wooly. |
| Sabouraud-maltose agar plate | A moderately fast growing colony is flat and entire-edged. The flat surface is velvety to powdery as conidia develop. | A white, flat, slightly folded colony is formed. The texture is velvety. Reverse color is not developed. |
| Mycological agar plate | The colony is heaped and has a depressed center. The texture is velvety. Reverse color is dark brown. | The colony is light pink, flat, velvety and scallop-edged. As conidia develop, a depressed dark green central zone is formed. Reverse color is orange. Red-brown pigment is produced. |
| Wort agar plate | A slow growing colony is brown, flat with slightly raised center and entire-edged. The texture is velvety. | A moderately fast growing colony is flat, scallop-edged, pink and has a depressed center. The texture is velvety. The reverse color is orange. No pigment is produced. |
| Corn meal agar plate | This organism has a slow growth rate with a colony that is first brownish white and membranous then a white and powdery center appears. | This organism has a moderately fast growth rate with a colony that is flat and entire-edged. Dark green conidia are produced abundantly. |
| Yeast extract-malt extract (YM) agar plate | This organism has an intermediate growth rate with a colony that is white gray and heaped. The texture is velvety and becomes powdery as conidia develop. | This organism has an intermediate growth rate with a colony that is flat, light brown, and scallop-edged. As conidia develop, the central zone becomes dark green. The reverse color is brown. |

TABLE II.

Physiological Properties

| Variable | Strain | |
|---|---|---|
| | Humicola spp. ATCC 20620 | Monocillium spp. ATCC 20621 |
| Oxygen | Aerobic. No anaerobic growth in YM borth. | Aerobic. No anaerobic growth in YM broth. |
| Temperature for growth | Good growth at 26–32° C., maximum temperature usually between 38–42° C., no growth at 45° C. or higher, slight growth at 5° C. after 7 days of cultivation on YM agar slant. | Good growth at 28–30° C., maximum temperature usually between 37–40° C., no growth at 42° C. or higher, slight growth at 5° C. after 5 days of cultivation on YM agar slant. |
| pH for growth | Optimum pH between 6.5–8.0, and no growth at pH 3.0 or less | Optimum pH between 7.5–8.5, and no growth at 4.0 or less. |
| Carbohydrate utilization | Growth on arabinose, xylose, glucose, mannose, galactose, fructose, lactose, maltose, sucrose, melibiose, raffinose, salicin, dulcitol, adonitol, erythritol, inositol, rhamnose, xylan, inulin, dextrin, starch and cellulose. | Growth on arabinose, xylose, glucose, mannose, galactose, fructose, lactose, maltose, sucrose, melibiose, raffinose, salicin, dulcitol, adonitol, inositol, rhamnose, xylan, inulin, dextrin, starch and cellulose. |

TABLE II.-continued

| | Physiological Properties | |
|---|---|---|
| | Strain | |
| Variable | Humicola spp. ATCC 20620 | Monocillium spp. ATCC 20621 |
| | No growth on levulose and trehalose. | No growth on levulose and erythritol. |

The oxidation of rifamycin B to rifamycin O can be carried out at any normal pH and temperature. However, considering the stability of the enzyme, the reaction is preferably conducted at a temperature less than about 60° C., and optimally between 30° C. to 40° C., and at a pH range of about 4 to 10. Selection of the reaction pH depends upon the relative enzyme activity at the selected pH and the type of the desired product. The maximum enzyme activity is found at pH 7.5 to 8.5 for Humicola spp. (ATCC 20621) while the predominating product is rifamycin O at pH 4 to 6 and rifamycin S at pH 7.0 and higher. The predominance of rifamycin O at acidic pH is ascribed to its insolubility in water at this pH. Rifamycin O is relatively soluble in water at alkaline pH, in which it hydrolyzes to rifamycin S. The desired product can be obtained by these two microbial enzymes by controlling the reaction pH sacrificing the catalytic efficiency of the respective enzyme.

The degree of enzyme reaction can be determined by thin layer chromatography (TLC) using Eastman Chromagram Sheet No. 13181 and a developing solvent of chloroform/acetone (1:1) mixture. The end point of reaction at acidic pH is confirmed by the complete disappearance of rifamycin B spot (yellow, Rf 0–0.1) which accompanies the intensification of the rifamycin O spot (pale yellow, Rf 0.6). At alkaline pH, the reaction proceeds with the initial appearance of rifamycin O (Rf 0.6) followed by the gradual intensification of rifamycin S spot (purple, Rf 0.4). For the preparative purpose of rifamycin S, the end point is when both the rifamycin B and the rifamycin O spots completely disappear while only the rifamycin S spot remains. If desired, after the hydrolysis of rifamycin O to rifamycin S, rifamycin SV can be obtained by reduction of rifamycin S with ascorbic acid. Rifamycin O and rifamycin S are usually obtained as precipitates and can be recovered from the reaction mixture through filtration or centrifugation. Rifamycin SV has a slightly higher solubility in neutral water than either rifamycin O or rifamycin S, and therefore, the recovery can be maximized at acidic pH. It can be easily effected by addition of an acid such as hydrochloric acid or acetic acid. The resulting yellow precipitate of rifamcyin SV can be recovered by filtration or centrifugation.

The following examples will further illustrate the present invention.

EXAMPLE 1

(a) Fermentation—One liter of the aqueous medium consisting of lyophilized corn steep liquor (2%), sobyean meal (1%), and yeast extract (0.5%), adjusted to pH 7.0 was added to a small fermentor and autoclaved. After cooling, 50 ml of seed culture obtained by growing Monocillium spp. (ATCC 20621) on the same medium for 2 days at 30° C. was added. It was cultivated for 3 days at 30° C. with an aeration speed 0.5 VVM and agitation speed 300 rpm.

(b) Preparation of enzyme—The culture broth was pooled and the whole cells were recovered through filtration. The cells are disrupted by sonication for 10 minutes. The supernatant after centrifugation at 10,000 rpm for 30 minutes was recovered and stored at 4° C.

(c) Reaction—Ten mililiters of cell extract were added to 500 ml of 0.1% rifamycin B solution (10 mM acetate buffer, pH 5.5). During reaction at 45° C. with aeration and agitation. The reaction solution became cloudy due to the formation of rifamycin O precipitate. The end point was detected by the formation of pale yellow spot ($R_f$ 0.6) of rifamycin O with complete disappearance of rifamycin B spot ($R_f$ 0–0.1, yellow) in TLC. The reaction was completed within 5 hours. After suction filtration on a Whatmann No. 1 filter paper, the precipitate was recovered and dried over sodium sulfate. By this process, 0.45 gr of rifamycin O (purity 98%) was obtained (yield=96%).

EXAMPLE 2

(a) Fermentation—Ten 500 ml Erlenmeyer flasks, each containing 100 ml of the aqueous medium consisting of glucose (1%), casein hydrolyzate (1%), yeast extract (1%), and $CuSO_4.5H_2O$ (0.005%) were adjusted to pH and autoclaved. After cooling, each flask was inoculated with one platinum wire loop of a meat extract agar slant culture of Humicola spp. (ATCC 20620). The inoculums were then cultivated for 4 days at 28° C. with shaking (6 cm stroke, 200 rpm).

(b) Recovery of whole cell—The culture broth was pooled and the whole cells were recovered by centrifugation at 3,000 rpm for 10 minutes. The cell pastes can be preserved at 4° C. for one month without substantial loss of enzyme activity.

(c) Enzyme reaction—Two grams of wet cell paste were added to 500 ml of 0.1% rifamycin B solution (10 mM phosphate buffer, pH 7.8). During the reaction at 37° C. with agitation and aeration, the color was gradually changed from the initial yellow color of rifamycin B to the purple color of rifamycin S. After reaction for 8 hours, the reaction was completed as confirmed by the complete disappearance of rifamycin B spot (yellow, Rf 0–0.1) in TLC using chloroform/acetone (1:1) mixture as a developing solvent. After separating the cells through filtration in a micropore sintered glass filter, the filtrate was centrifuged at 10,000 rpm for 20 minute while maintaining the temperature at 4° C. By drying the precipitate over sodium sulfate, 0.4 gr of crude rifamycin S was obtained. Recrystallization from methanol-water (1:1) (pH 2.5) gave 0.38 gr of rifamycin S (yield=93%).

EXAMPLE 3

(a) Fermentation—Twenty-two liters of the aqueous medium consisting of lactose (1.5%), peptone (1%), and yeast extract (0.5%) were adjusted to pH 7.0 before and after sterilization for 30 minutes at 121° C. in a 28 l jar fermentor. It was inoculated with 1 l of a culture of Humicola spp. (ATCC 20620) which has been grown at 30° C. for 2 days in the same medium. It was cultivated for 3 days at 30° C. with agitation (400 rpm) and aeration (0.3 VVM).

(b) Enzyme immobilization—The whole cells recovered by continuous centrifugation were ruptured by homogenization with seasand. The cell extract was obtained through suction filtration, and treated with 100 gr of celite for 30 minutes with vigorous agitation. During this procedure, the enzyme was completely adsorbed to celite. The residual enzymes were able to be recovered by treating the filtrate with 10 gr of celite. After washing the celite cake with 500 ml of distilled water, 210 gr of wet slurry were obtained. The cake was preserved in a refrigerator at 4° C.

(c) Reaction—Ten grams of the enzyme adsorbed on celite were added to 300 ml of 1% rifamycin B solution (10 mM phosphate buffer, pH 8.5). The conversion to rifamycin S was completed in 7 hours of reaction at 40° C. with aeration and agitation. The celite filter cake recovered by filtration on a sintered glass was washed with 200 ml of methanol. The final methanolic aqueous solution of rifamycin S was warmed to 50° C. in order to solubilize completely the residual rifamycin S precipitate. 30 ml of 5% ascorbic acid solution in water was added thereto dropwisely while continuous stirring. The purpose color of rifamycin S was gradually changed to the deep red color of rifamycin SV. After adjusting the final pH to 4.0, the methanol was completely evaporated using suction evaporator at 40° C. Afte chilling the final solution at 4° C. for 2 days, the rifamycin SV crystals were recovered by filtration. 2.4 gr of deep yellowish rifamycin SV crystals were obtained after drying over sodium sulfate (yield=87%).

EXAMPLE 4

(a) Fermentation—Seventy liters of aqueous medium consisting of glycerin (2%), soybean meal (1.5%), ammonium acetate (1%), ZnSO4 (0.001%), and CuSO4 (0.005%) were adjusted to pH 7.0 and autoclaved for 30 minutes at 121° C. in a 100 l capacity fermentor. After cooling, 3 l of a culture of Monocillium spp. (ATCC 20621) was inoculated which has been grown at 35° C. for 1.5 days on the same medium. It was cultivated for 3 days at 35° C. controlling the pH to 7.0 throughout cultivation with an aeration speed 0.5 VVM and agitation speed 300 rpm.

(b) Enzyme immobilization—The whole cells were recovered through continuous centrifugation. 100 gr of wet cell paste were treated with 500 ml of acetone for defatting. Five grams of acetone-dried powder thus prepared were added to 20 ml of acrylamide solution in 0.1 M Tris-HCl buffer (pH 7.0) composed of 9.5 gr of acrylamide monomer and 0.5 g of bis-acrylamide. After completely mixing, 2 ml of TEMED and 0.5 g of ammonium persulfate were added for polymerization while maintaining the temperature at 40° C. After the gel was extruded through a sieve (mesh size 16), it was cut into a suitable size (205 mm) followed by an extensive wash with 500 ml of distilled water.

(c) Reaction—Ten grams (wet weight) of acrylamide gel entrapped cell were added to 500 ml of 0.1% rifamycin B solution (pH 5.0). After reaction for 6 hours at 30° C. with stirring and aeration, the immobilized enzyme was recovered by filtration followed by a wash with 100 ml of acetone. The immobilized enzyme was stored at 4° C. for further use. The filtrate was suction evaporated at 40° C. to removed acetone and chilled to 4° C. for one day, in which pale yellowish crystals of rifamycin O were gradually formed. After filtration and drying, 0.47 gr of product was obtained (yield=93%).

EXAMPLE 5

Ten grams of acrylamide gel entrapped enzyme which were recovered in Example 4 were then added to 200 ml of 0.5% rifamycin B solution (pH 8.0). Rifamycin B was completely converted to rifamycin S during a 10 hour reaction period. The immobilized enzyme pellet was recovered by filtration followed by wash with 50 ml of acetone. After evaporation of acetone at 40° C., the reaction solution was chilled to 4° C. for one day. The purple precipitate was recovered through centrifugation at 10,000 rpm for 30 minutes and, dried. 8.8 gr of rifamycin S (Na+ form) were obtained (yield=93%).

EXAMPLE 6

Five grams of the celite-adsorbed enzyme of Humicola spp. (ATCC 20620), which had been recovered during the reaction in Example 3, were added to 500 ml of 0.1% rifamycin B solution (pH 5.0) and stirred for 4 hours at 40° C. with aeration. The celite cake was recovered by filtration on a sintered glass followed by wash with 50 ml of acetone. After evaporation of acetone by a suction evaporator at 30° C., the solution was chilled to 4° C. for one day. After filtration and drying, 0.45 gr of rifamycin O was obtained (yield=90%).

EXAMPLE 7

Fifty grams (wet weight) of whole cells of Monocillium spp. (ATCC 20621), obtained through the procedure described in Example 2, were added to 2 l of diluted cell-free rifamycin B fermentation broth (1,020 mg rifamycin B/l) obtained by culture of Nocardia mediterranei N-1. After adjusting the pH to 5.5, the enzyme reaction was carried out at 40° C. with aeration and agitation. After reaction for 3 hours, the crude rifamycin O slurry obtained by filtration was dried to give 2.8 gr of crude rifamycin O (purity 70%). The overall recovery yield was 95%.

EXAMPLE 8

Two hundred grams (wet weight) of whole cell of Humicola spp. (ATCC 20620) obtained through Example 1, were added to 3 l of centrifuged rifamycin B fermentation broth (5050 mgr rifamycin B/l). Adjusting the broth pH to 8.2, it was agitated with aeration for 8 hours. Conversion to rifamycin S was accompanied by a color change to deep red. After the reaction was completed, the crude rifamycin S was recovered through filtration on a sintered glass followed by an extensive wash with 300 ml of acetone. By evaporaion of acetone and chilling to 4° C., 18.9 gr of crude rifamycin S (Na+ form) were obtained (Purity=74%, Yield=92.3%.

EXAMPLE 9

Fifty grams (wet weight) of acrylamide gel entrapped cell of Monocillium spp. (ATCC 20621), prepared through the procedures described in Example 4, were added to 2 l of centrifuged rifamycin B fermentation broth (6100 mgr rifamycin B/l). After reaction at 45° C. for 25 hours were aeration and agitation, the immobilized enzyme pellets were recovered through filtration on a sintered glass. It was extensively washed with 500 ml of acetone. The residual precipitates were completely solubilized by addition of another 500 ml of acetone. Thereto, 100 ml of ascorbic acid solution (10% in water) were added dropwisely while gently stirring.

After confirming complete reduction to rifamycin SV, the pH was adjusted to 3.5 and the acetone was removed by evaporation with suction at 40° C. The solution was chilled to 4° C. for one day and the yellowish precipitate thus formed was recovered through filtration and dried. By this procedure, 12.5 gr of crude rifamycin SV were obtained (Purity=84%, Yield=93.8%).

EXAMPLE 10

The immobilized enzyme of Monocillium spp. (ATCC 20621) was prepared by adsorbing the enzyme on bentonite, as described in Example 3. Thrity grams of the immobilized enzyme thus prepared were added to 2 l of rifamycin B fermentation broth (6200 mgr rifamycin B/l broth) previously adjusted to pH 9.0, and the mixture was continuously agitated for 16 hours at 45° C. with aeration. The immobilized enzyme was recovered by filtration on a sintered glass, and then washed with 500 ml of methanol. After complete solubilization of rifamycin S precipitate by adding another 500 ml of methanol, the pH was adjusted to 3.0 with 10% HCl. Suction evaporation of methanol at 30° C. and chilling to 4° C. for one day gave 13.7 gr of crude rifamycin S (H+ form). The purity of the final product was 78% (Yield=93.7%).

EXAMPLE 11

The acetone-dried enzyme of Humicola spp. (ATCC 20620) was entrapped in acrylamide gel by the procedure described in Example 4. Fifty grams (wet weight) of the immobilized enzyme pellets thus prepared were added to 3 l of diluted rifamycin B fermentation broth (1200 mgr rifamycin B/l broth) previously adjusted to pH 5.5 followed by agitation and aeration at 40° C. After 4 hours of reaction, the immobilized enzyme pellets were recovered by filtration on a sintered glass filter and then washed with 300 ml of methanol. The filtrate was adjusted to pH 3.0 with 10% HCl and extracted with 500 ml of chloroform. The organic layer was concentrated to complete dryness. By this procedure, 3.4 gr of rifamycin O were obtained (Purity=96%, Yield=91%).

The above description has been prepared for the purpose of enabling those people skilled in the art to practice the present invention and has not attempted to describe all the possible modifications and variations of the invention which will become apparent to the person skilled in the art upon reading this disclosure. It is intended, however, that all such modifications and variations be included within the scope of the present invention which is defined by the following claims.

What is claimed is:

1. A process for the enzymatic conversion of rifamycin B to oxidized derivatives thereof comprising subjecting rifamycin B to the action of a microbial oxidation enzyme derived from Humicola spp. (ATCC 20620) or Monocillium spp. (ATCC 20621) capable of converting rifamycin B to an oxidized derivative thereof in the presence of oxygen at a pH of from 4 to 10, and recovering an oxidized derivative of rifamycin B.

2. The process according to claim 1 wherein said enzyme is one selected from the group consisting of microbial cells, cell extract, and immobilized enzymes.

3. The process according to claim 1 or 2, wherein said reaction is carried out at a pH ranging from 4 to 6 to yield rifamycin O.

4. The process according to claim 1 or 2, wherein said reaction is carried out at a pH ranging from 7 to 9 to yield rifamycin S.

5. The process according to claim 4, wherein rifamycin S is further reduced to rifamycin SV in the presence of ascorbic acid.

6. The precess of claim 1, wherein the microbial oxidation enzyme is derived from Humicola spp.

7. The process of claim 1, wherein the microbial oxidation enzyme is derived from Monocillium spp.

* * * * *